United States Patent
Zhang et al.

(10) Patent No.: US 12,226,446 B2
(45) Date of Patent: Feb. 18, 2025

(54) WS-635 USES THEREOF IN MEDICINE

(71) Applicants: WATERSTONE PHARMACEUTICALS(WUHAN) CO., LTD., Hubei (CN); THE GENERAL HOSPITAL CORPORATION, Boston, MA (US)

(72) Inventors: Faming Zhang, Hubei (CN); Jian Cui, Hubei (CN); Yao Yu, Hubei (CN); Minglong Hu, Hubei (CN); Zhongcong Xie, Andover, MA (US)

(73) Assignees: WATERSTONE PHARMACEUTICALS(WUHAN) CO., LTD., Hubei (CN); THE GENERAL HOSPITAL CORPORATION, Boston, MA (US)

( * ) Notice: Subject to any disclaimer, the term of this patent is extended or adjusted under 35 U.S.C. 154(b) by 857 days.

(21) Appl. No.: 17/429,667

(22) PCT Filed: Oct. 11, 2019

(86) PCT No.: PCT/CN2019/110576
§ 371 (c)(1),
(2) Date: Aug. 10, 2021

(87) PCT Pub. No.: WO2021/068188
PCT Pub. Date: Apr. 15, 2021

(65) Prior Publication Data
US 2022/0105149 A1    Apr. 7, 2022

(51) Int. Cl.
*A61K 38/13*    (2006.01)
*A61P 25/00*    (2006.01)

(52) U.S. Cl.
CPC .............. *A61K 38/13* (2013.01); *A61P 25/00* (2018.01)

(58) Field of Classification Search
None
See application file for complete search history.

(56) References Cited

U.S. PATENT DOCUMENTS

| 11,845,809 B2* | 12/2023 | Cui | C07K 7/645 |
| 11,993,664 B2* | 5/2024 | Cui | A61K 31/4178 |
| 2010/0173837 A1* | 7/2010 | Hopkins | A61P 31/18 |
| | | | 514/2.4 |

FOREIGN PATENT DOCUMENTS

| WO | 2012075494 | 6/2012 |
| WO | 2014145686 | 9/2014 |

OTHER PUBLICATIONS

Deiner S, Silverstein JH. Postoperative delirium and cognitive dysfunction. Br J Anaesth. Dec. 2009; 103 Suppl 1(Suppl 1):i41-46. doi: 10.1093/bja/aep291. PMID: 20007989; PMCID: PMC2791855. (Year: 2009).*
Tencate V, Sainz B Jr, Cotler SJ, Uprichard SL. Potential treatment options and future research to increase hepatitis C virus treatment response rate. Hepat Med. Oct. 2010;2010(2):125-145. doi: 10.2147/HMER.S7193. PMID: 21331152; PMCID: PMC3039485. (Year: 2010).*
Kirchmair, J., Gä¶ller, A., Lang, D. et al. Predicting drug metabolism: experiment and/or computation ?. Nat Rev Drug Discov 14, 387-404 (2015). https://doi.org/10.1038/nrd4581 (Year: 2015).*
WIPO, International Search Report for PCT/CN2019/110576, Jul. 15, 2020.

* cited by examiner

*Primary Examiner* — Christina Bradley
(74) *Attorney, Agent, or Firm* — Hodgson Russ LLP

(57) ABSTRACT

The present invention relates to a method of treating, preventing, or lessening postoperative cognitive dysfunction (POCD) in a subject in need thereof, the method comprising the step of administering to the subject a therapeutically effective amount of a compound of Formula I or a stereoisomer, a tautomer, an N-oxide, a solvate, a metabolite, a pharmaceutically acceptable salt or a prodrug thereof, (I)

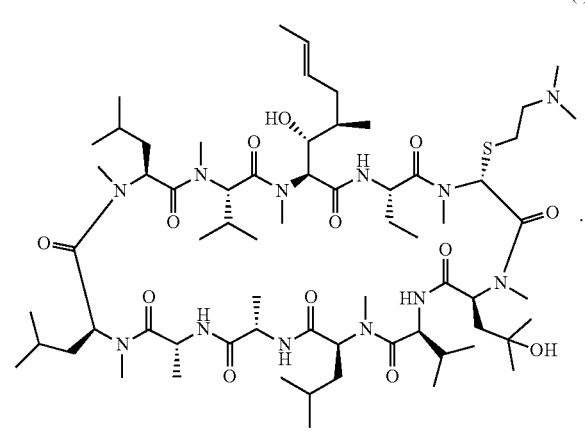

17 Claims, 15 Drawing Sheets

Righting Reflex

WS-635 USES THEREOF IN MEDICINE

CROSS-REFERENCE TO RELATED APPLICATION

This application is a U.S. national phase application of International Application No. PCT/CN2019/110576, filed on Oct. 11, 2019, the entire disclosure of which is incorporated herein by reference.

FIELD OF THE DISCLOSURE

The present invention belongs to the field of medicine. Specifically, it relates to the uses of (3S,6S,9S,12R,15S,18S,21S,24S,27R,30S,33S)-27-((2-(dimethylamino)ethyl)thio)-30-ethyl-33-((1R,2R,E)-1-hydroxy-2-methylhex-4-en-1-yl)-24-(2-hydroxy-2-methylpropyl)-6,9,18-tri isobutyl-3,21-diisopropyl-1,4,7,10,12,15,19,25,28-nonamethyl-1,4,7,10,13,16,19,22,25,28,31-undecaazacyclotritriacontan-2,5,8,11,14,17,20,23,26,29,32-undecaone (I) (WS-635, also known as SCY-635) and pharmaceutically compositions thereof in the manufacture of a medicament for preventing, managing, treating or lessening postoperative cognitive dysfunction (POCD) in a patient.

BACKGROUND OF THE INVENTION

WS-635 (the compound of formula (I)) is a novel non-immunosuppressive cyclosporine-based analog that exhibits potent suppression of hepatitis C virus (HCV) replication in vitro. WS-635 inhibited the peptidyl prolyl isomerase activity of cyclophilin A at nanomolar concentrations but showed no detectable inhibition of calcineurin phosphatase activity at concentrations up to 2 µM. Metabolic studies indicated that WS-635 did not induce the major cytochrome P450 enzymes 1A2, 2B6, and 3A4. WS-635 was a weak inhibitor and a poor substrate for P-glycoprotein. Functional assays with stimulated Jurkat cells and stimulated human peripheral blood mononuclear cells indicated that WS-635 is a weaker inhibitor of interleukin-2 secretion than cyclosporine. A series of two-drug combination studies was performed in vitro. WS-635 exhibited synergistic antiviral activity with alpha interferon 2b and additive antiviral activity with ribavirin. WS-635 was shown to be orally bioavailable in multiple animal species and produced blood and liver concentrations of parent drug that exceeded the 50% effective dose determined in the bicistronic con1b-derived replicon assay. These results suggest that WS-635 warrants further investigation as a novel therapeutic agent for the treatment of individuals who are chronically infected with HCV.

Every year, over 312 million patients worldwide have surgery under anesthesia. Postoperative cognitive dysfunction (POCD) is one of the most common postoperative complications in geriatric patients. They have independent adverse effects on long-term morbidity, mortality, the cost of healthcare, and quality of life.

Post-Operative Cognitive Dysfunction (POCD) is a common complication, especially in the elder, after cardiac or non-cardiac surgery (e.g., hip replacement) with general anesthesia. POCD is a disorder including deterioration in memory, attention and speed of information processing. It can be chronic and devastating for post-operative recovery of patients. There are over 2.5 million such surgical procedures annually in North America with an incidence of POCD of over 30%.

There is now substantial evidence that many elderly patients experience cognitive deterioration postoperatively. In a prospective, randomized trial of general vs epidural anesthesia with sedation for total knee replacement in patients >70 yr of age, cognitive performance, as assessed with psychometric tests, was worse than the preoperative baseline in 4-6% of patients six months after anesthesia and surgery. Another large, prospective, controlled international study demonstrated a cognitive dysfunction in 9.9% of patients three months postoperatively whereas only about 3% of the age-matched controls were similarly impaired. Among patients over 75 yr of age, 14% had a persistent cognitive dysfunction after general anesthesia and surgery.

Further, a recent study by Wilder et al. investigated more than 5,000 children and reported that children who had early exposure to anesthesia were at an increased risk for developing a learning disability. While there is no direct evidence for a causal relationship between anesthesia administration and later learning-related outcomes, the risk for the development of a learning disability increases with longer cumulative duration of anesthesia exposure. Another pilot study by Kalkman et al. has also discussed that children who underwent surgery and anesthesia at younger than 2 yr could be at an increased risk of developing a deviant behavior later in life. These findings discuss that anesthesia can be a significant risk factor for later development of a learning disability and deviant behavior.

Indeed, no adequate treatment options has yet existed for this distressing postsurgical and post-anesthesia event. Even the advent of newer short-acting anesthetic medicines does not alleviate the post-anesthetic effects on the patients. As the incidence of POCD remains high and such disorder is devastating for the post-operative discovery of patients, discovery of neuropathogenesis of POCD and thus therapeutic interventions for POCD would be urgently needed for reducing healthcare cost and improving quality of life management. As such, there is a strong need for simple and effective methods to prevent and/or treat POCD.

SUMMARY OF THE DISCLOSURE

The following just summarizes some aspects of the invention, but are not limited to these. These aspects and other parts will be described more completely later. All references of this specification are incorporated herein by reference in their entirety. Where there are differences between disclosure of the present specification and cited references, the disclosure of the present specification controls.

In the research and development process, the inventors surprisingly found that WS-635 could significantly attenuate the isoflurane-induced cognitive impairment in mice. The inventors further investigated that the WS-635 could be used to treat postoperative cognitive dysfunction (POCD). WS-635 as the active ingredient of the postoperative cognitive dysfunction therapeutic agents has no immunosuppressive effects and has less toxic effects. Moreover, WS-635 has better stability, pharmacokinetics etc., and WS-635 has already been shown to be more effective in treating POCD.

Specifically, in one aspect, the present invention relates to a method of treating, preventing, or lessening postoperative cognitive dysfunction (POCD) in a subject in need thereof, the method comprising the step of administering to the subject a therapeutically effective amount of a compound of Formula I or a stereoisomer, a tautomer, an N-oxide, a solvate, a metabolite, a pharmaceutically acceptable salt or a prodrug thereof,

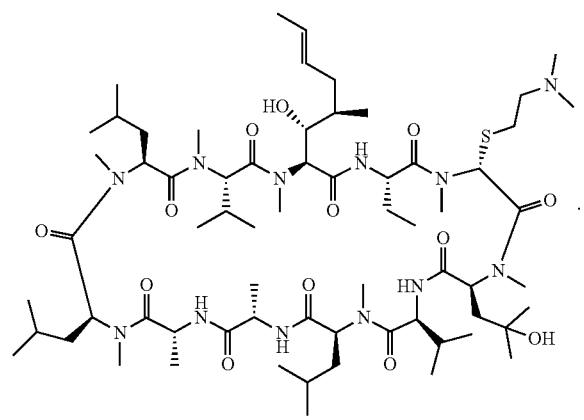

(I)

In the research and development process, the inventors surprisingly found that WS-635 could attenuate the anesthesia/surgery-induced cognitive impairment in mice with dose-dependent manner without affecting the potency of the anesthetics. Furthermore, the inventors surprisingly found that WS-635 could attenuate the anesthesia/surgery-induced changes in brain levels of IL-6, ROS, ATP, synaptophysin and PSD-95. According to the examples of present disclosure, the said compound of formula (I) can rescue the anesthesia/surgery-induced cognitive impairment and have amazingly good effect on preventing, treating or lessening postoperative cognitive dysfunction.

In one embodiment, the postoperative cognitive dysfunction is isoflurane-induced, desflurane-induced, sevoflurane-induced or propofol-induced.

In one embodiment, the compound is administered to the subject within 48 hours prior to the operation.

In one embodiment, the compound is administered to the subject within 24 hours prior to the operation.

In one embodiment, the compound is administered to the subject within 48 hours after the operation.

In one embodiment, the compound is administered to the subject within 24 hours after the operation.

In one embodiment, the compound is administered at a daily dose of less than about 900 mg.

In one embodiment, the compound is administered at a daily dose of between about 10 to about 900 mg.

In one embodiment, the compound is administered at a daily dose of between about 50 to about 600 mg.

In one embodiment, the compound is administered 1 time per day.

In one embodiment, the compound is administered 1 time per day as a single dosage.

In one embodiment, the compound is administered by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intraperitoneally and intrathecally.

In one embodiment, the compound is administered orally or intravenously.

In one embodiment, the compound is administered in a form of tablet, capsule or injection.

In one embodiment, the compound is administered in combination with one or more other agent used for preventing, treating or lessening cognitive impairment other than the compound of Formula I.

In one embodiment, the other agent is selected from the group consisting of at least one member of coenzymes, such as coenzyme $Q_{10}$.

In another aspect, provided herein is a compound of Formula I or a stereoisomer, a tautomer, an N-oxide, a solvate, a metabolite, a pharmaceutically acceptable salt or a prodrug thereof, for use in treating, preventing, or lessening postoperative cognitive dysfunction (POCD) in a subject in need thereof, (I)

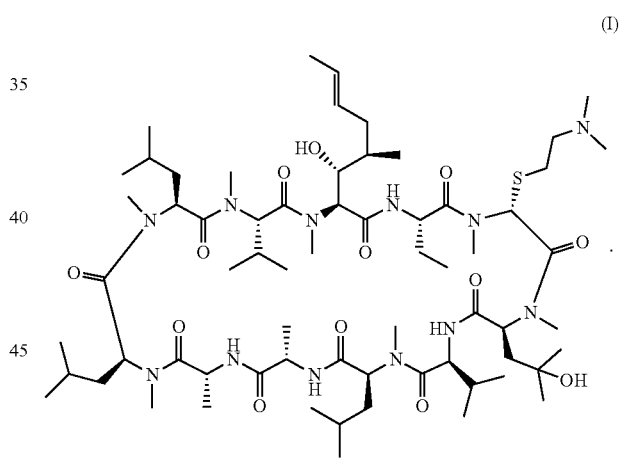

As described above, the said compound of formula (I) can rescue the anesthesia/surgery-induced cognitive impairment and have amazingly good effect on preventing, treating or lessening postoperative cognitive dysfunction without affecting the potency of the anesthetics.

In one embodiment, the postoperative cognitive dysfunction is isoflurane-induced, desflurane-induced, sevoflurane-induced or propofol-induced.

In one embodiment, the compound is administered to the subject within 48 hours prior to the operation.

In one embodiment, the compound is administered to the subject within 24 hours prior to the operation.

In one embodiment, the compound is administered to the subject within 48 hours after the operation.

In one embodiment, the compound is administered to the subject within 24 hours after the operation.

In one embodiment, the compound is administered at a daily dose of less than about 900 mg.

In one embodiment, the compound is administered at a daily dose of between about 10 to about 900 mg.

In one embodiment, the compound is administered at a daily dose of between about 50 to about 600 mg.

In one embodiment, the compound is administered 1 time per day.

In one embodiment, the compound is administered 1 time per day as a single dosage.

In one embodiment, the compound is administered by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intraperitoneally and intrathecally.

In one embodiment, the compound is administered orally or intravenously.

In one embodiment, the compound is administered in a form of tablet, capsule or injection.

In one embodiment, the compound is administered in combination with one or more other agent used for preventing, treating or lessening cognitive impairment other than the compound of Formula I.

In one embodiment, the postoperative cognitive dysfunction is isoflurane-induced, desflurane-induced, sevoflurane-induced or propofol-induced.

In another aspect, provided herein is a pharmaceutical composition comprising a therapeutically effective amount of a compound of Formula I or a stereoisomer, a tautomer, an N-oxide, a solvate, a metabolite, a pharmaceutically acceptable salt or a prodrug thereof,

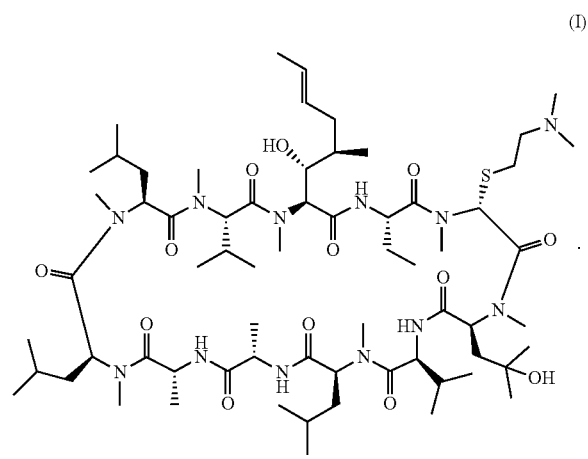 [SMILES: C/C=C/C[C@@H](C)[C@@H](O)[C@H]1C(=O)N[C@@H](CC)C(=O)N(C)[C@H](SCCN(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

(I)

In one embodiment, the composition is formulated in a single dose form wherein such single dose form comprises less than 900 mg of Compound I.

In one embodiment, such single dose further comprise one or more other agent used for preventing, treating or lessening cognitive impairment other than the compound of Formula I.

In one embodiment, the other agent is selected from the group consisting of at least one member of coenzymes such as coenzyme $Q_{10}$.

In another aspect, provided herein is use of a compound of Formula I or a stereoisomer, a tautomer, an N-oxide, a solvate, a metabolite, a pharmaceutically acceptable salt or a prodrug thereof in treating, preventing, or lessening postoperative cognitive dysfunction (POCD) in a subject in need thereof,

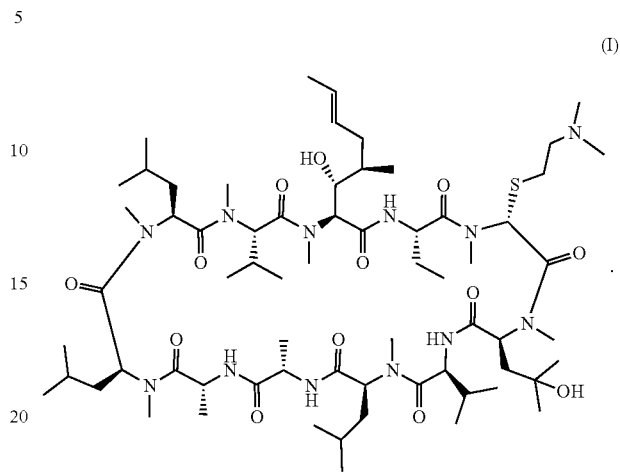

(I)

In one embodiment, the postoperative cognitive dysfunction is isoflurane-induced, desflurane-induced, sevoflurane-induced or propofol-induced.

In one embodiment, the compound is administered to the subject within 48 hours prior to the operation.

In one embodiment, the compound is administered to the subject within 24 hours prior to the operation.

In one embodiment, the compound is administered to the subject within 48 hours after the operation.

In one embodiment, the compound is administered to the subject within 24 hours after the operation.

In one embodiment, the compound is administered at a daily dose of less than about 900 mg.

In one embodiment, the compound is administered at a daily dose of between about 10 to about 900 mg.

In one embodiment, the compound is administered at a daily dose of between about 50 to about 600 mg.

In one embodiment, the compound is administered 1 time per day.

In one embodiment, the compound is administered 1 time per day as a single dosage.

In one embodiment, the compound is administered by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intraperitoneally and intrathecally.

In one embodiment, the compound is administered orally or intravenously.

In one embodiment, the compound is administered in a form of tablet, capsule or injection.

In one embodiment, the compound is administered in combination with one or more other agent used for preventing, treating or lessening cognitive impairment other than the compound of Formula I.

In one embodiment, the postoperative cognitive dysfunction is isoflurane-induced, desflurane-induced, sevoflurane-induced or propofol-induced.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DESCRIPTION OF THE DISCLOSURE

Definitions and General Terminology

Figure 1:
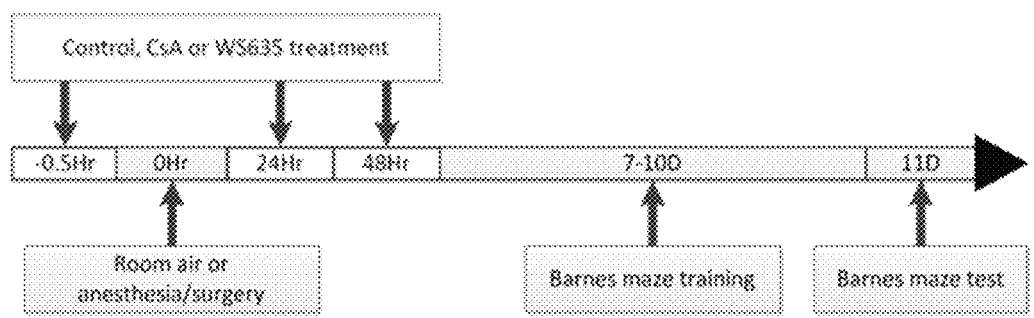
FIG. 1 shows the diagram of the experimental design (Barnes Maze Test)

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all scientific and technical terms used herein have the same meaning as is commonly understood by one skilled in the art to which this invention belongs. All patents and publications referred to herein are incorporated by reference in their entirety.

The grammatical articles "a", "an" and "the", as used herein, are intended to include "at least one" or "one or more" unless otherwise indicated herein or clearly contradicted by the context. Thus, the articles used herein refer to one or more than one (i.e. at least one) of the grammatical objects of the article. For example, "an embodiment" refers to one or more embodiments.

The term "comprise" is an open expression, it means comprising the contents disclosed herein, but don't exclude other contents.

The term "pharmaceutically acceptable" as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C1-24) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, each of which is incorporated herein by reference.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4} \text{ alkyl})_4$ salts. This invention also envisions the quaternization of any basic nitrogen-containing groups of the compounds disclosed herein. Water or oil soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, ethanolamine and the mixture thereof. The term "hydrate" refers to the complex where the solvent molecule is water.

The term "hydrate" can be used when said solvent is water. In one embodiment, one water molecule is associated with one molecule of the compounds disclosed herein, such as a hydrate. In another embodiment, more than one water molecule may be associated with one molecule of the compounds disclosed herein, such as a dihydrate. In still another embodiment, less than one water molecule may be associated with one molecule of the compounds disclosed herein, such as a hemihydrate. Furthermore, all the solvates of the invention retain the biological effectiveness of the non-hydrate form of the compounds disclosed herein.

As used herein, the term "therapeutically effective amount" or "therapeutically effective dose" refers to the amount of compound disclosed herein that can elicit the biological or medical response (such as reducing or inhibiting the activity of an enzyme or protein, or improving symptoms, lessening disorders, slowing or delaying the development of diseases and the like).

Pharmaceutical Composition of the Compound and Preparations and Administration

In one aspect, provided herein is a pharmaceutical composition including compound of Formula (I) or a stereoisomer, a tautomer, an N-oxide, a solvate, a metabolite, a pharmaceutically acceptable salt or a prodrug thereof. The pharmaceutical compositions further comprise at least a pharmaceutically acceptable carrier, an adjuvant, or an excipient, and optionally other therapeutic and/or prophylactic ingredients.

Suitable carriers, adjuvants and excipients are well known to those skilled in the art and described in detail in such as Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. One skilled in the art will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

In certain embodiments, the subject at risk of POCD is a child or an elderly. In various embodiments, the subject is a mammal, e.g., a human.

The methods described herein can be used in temporal proximity to general anesthesia. With respect to general anesthesia, inhalational anesthetics and intravenous anesthetics can be used with the methods of the invention. Non-limiting examples of inhalational anesthetics include ethers such as diethyl ether, methoxypropane, vinyl ether, halogenated ethers, e.g., desflurane, enflurane, halothane, isoflurane, methoxyflurane; haloalkanes, such as chloroform, halothane, trichloroethylene, cyclopropane, ethylene, nitrous oxide, sevoflurane, xenon, deuterated isoflurane, hexafluoro-t-butyl-difluoromethyl ether, deutered analogues of methoxyflurane, deutered sevoflurane, and other inhalational anesthetic disclosed in the U.S. Patents, the content of all which is incorporated herein by reference in its entirety. Any of the inhalational anesthetics can be used alone or in combination with other medications to maintain anesthesia. For example, nitrous oxide can be used in combination with other inhalational anesthetics. Accordingly, in some embodiments of the methods, the compound of formula (I) can be administered to a subject in temporal proximity to at least one or a combination of isoflurane, desflurane, sevoflurane or propofol anesthetics.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable prodrugs, salts, esters, salts of such esters, or any other adduct or derivative which upon administration to a patient in need thereof is capable of providing, directly or indirectly, a compound as otherwise described herein, or a metabolite or residue thereof.

In one embodiment, the compounds disclosed herein can be prepared to oral dosage forms. In one embodiment, the compounds disclosed herein can be prepared to inhalation dosage forms. In one embodiment, the compounds disclosed herein can be prepared to dosage forms of nasal administration. In one embodiment, the compounds disclosed herein can be prepared to transdermal dosage forms. In one embodiment, the compounds disclosed herein can be prepared to dosage forms of topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Provided herein is a pharmaceutical composition which can be prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to 10 microns (for example as measured using laser diffraction).

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research*, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

The pharmaceutical compositions provided herein may be formulated as immediate or modified release dosage forms, including delayed-, sustained, pulsed-, controlled, targeted-, and programmed-release forms.

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

The pharmaceutical compositions provided herein may be co-formulated with other active ingredients which do not impair the desired therapeutic action, or with substances that supplement the desired action.

In one embodiment, the therapeutic methods disclosed herein comprise administrating to a patient in need of the treatment a safe and effective amount of the compound of the invention or the pharmaceutical composition containing the compound of the invention. Each example disclosed herein comprises treating the above disorders or diseases by administrating to a patient in need of the treatment a safe and effective amount of the compound of the invention or the pharmaceutical composition containing the compound of the invention.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In one embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

Compounds provided herein can used in combination with sedative, hypnotic, anxiolytic, antipsychotic, antianxiety agent, cyclopyrrolidone, imidazopyridine, pyrazolopyrimidines, minor tranquilizer, melatonin agonist and antagonist, melatoninergic agent, benzodiazepine, barbiturate, 5HT-2 antagonist, and the like. For example: adinazolan, allobarbital, alonimid, alprazolam, amitriptyline, amobarbital, amoxapine, bentazepam, tacitin, brotizolam, bupropion, buspirone, butabarbital, butalbital, capuride, carbocloral, chloral betaine, chloral hydrate, chlorodyne, clomipramine, clonazepam, domperidone, methaminodiazepoxide, cloretate, clozapine, cyprazepam, desipramine, dexclamo, diazepam, chloralsalicylamide, divalproic acid, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, orazepam, lormetazepam, maprotiline, mecloqualone, melatonin, methylphenobarbital, meprobamate, methaqualone, midaflur, midazolam, nefazodone, nisobamate, nitrazepam, nortriptyline, oxezepam, paraaldehyde, paroxetine, pentobarbital, perlapine, perphenazine, phenelzine, phenobarbital, Prazepam, promethazine, isopropylphenol, protriptyline, quazepam, reclazepam, rolipram, secobarbital, sertraline, suproclone, temazepam, thioridazine, tracazolate, tranylcypromine, trazodone, triazole benzodiazepine, trepipam, tricetamide, trichloroethyl phosphate, trifluoperazine, trimetozine, trimeprimine, uldazepam, venlafaxine, zaleplon, zolazepam, zolpidem and the salts and compositions thereof, and the like. Alternatively, physical methods such as light therapy or electrical stimulation can be used during administration of compounds disclosed herein.

Additionally, the compounds of Formula (I) may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Use of the Compounds and Pharmaceutical Compositions

Compounds WS-635 or pharmaceutical compositions disclosed herein are efficient for treating or preventing POCD without affecting the potency of the anesthetics.

Besides WS-635, the inventors found that Alisporivir, NIM811, CRV431 or NVP018 could also be used for treating POCD. The compounds or pharmaceutical compositions comprising the above compounds maybe efficient for treating or preventing POCD.

An "effective amount", "a therapeutically effective amount" or "effective dose" of the compound, or a stereoisomer, a tautomer, an N-oxide, a solvate, a metabolite, a pharmaceutically acceptable salt or a prodrug thereof or pharmaceutically acceptable composition disclosed herein is an amount that is effective in treating or lessening the severity of postoperative cognitive dysfunction. The complex and pharmaceutically acceptable compositions are effectively administered in a fairly wide dose range. For example, the daily dose is from about 0.1 mg to 900 mg per person, the compounds or pharmaceutically acceptable compositions can be administered in a single dose or in several divided doses a day. The compound and compositions, according to the method disclosed herein, may be administered using any amount and any route of administration which is effective for treating or lessening the severity of the postoperative cognitive dysfunction. The exact amount required will vary from subject to subject, depending on the species, age, and general condition of the subject, the severity of the infection, the particular agent, its mode of administration, and the like. The compound or pharmaceutical composition disclosed herein can also be administered with one or more other therapeutic agents as discussed above.

In some embodiments, the compound described herein can be administered to a subject within 48 hours prior to the operation or within 24 hours prior or within 1~24 hours prior to the operation under anesthesia and administered to the subject within 48 hours after the operation or within 24 hours or within 1~24 hours after the operation. The compound described herein can be administered at a daily dose of less than about 900 mg, for example, at a daily dose of between about 10 to about 900 mg or at a daily dose of between about 50 to about 600 mg. The compound can be administered 1 time per day or can be administered 1 time per day as a single dosage.

Besides being useful for human treatment, WS-635 and the compositions thereof are also useful for veterinary treatment of animals such as companion animals, exotic animals and mammals of farm animals. In other embodiments, the animals disclosed herein include horses, dogs, and cats. As used herein, the compounds disclosed herein include the pharmaceutically acceptable derivatives thereof.

EXAMPLES

Materials and Methods

Mice Anesthesia and Surgery 9-month-old C57BL/J6 female mice were adaptive in lab for 3 days. The mice were randomly assigned to the anesthesia/surgery group or control group by weight. The mice in the anesthesia/surgery group had a simple laparotomy under isoflurane anesthesia using the methods described in the inventors' previous studies (Ren Q, Peng M, Dong Y, et al. Surgery plus anesthesia induces loss of attention in mice. Front Cell Neurosci. 2015; 9: 346). Specifically, the inventors anesthetized each of the mice using 1.4% isoflurane in 100% oxygen in a transparent acrylic chamber. Fifteen minutes after the induction, the inventors moved the mouse out of the chamber. Isoflurane anesthesia was maintained via a cone device, and one 16-gauge needle was inserted into the cone near the nose of the mouse to monitor the concentration of isoflurane. The inventors made a longitudinal midline incision from the xiphoid to the 0.5 centimeter proximal pubic symphysis on the skin, abdominal muscles and peritoneum. The inventors then sutured the incision layer by layer with 5-0 Vicryl thread.

The inventors applied EMLA cream (2.5% lidocaine and 2.5% prilocaine) to the incision site at the end of the procedure, and then every eight hours until the euthanasia of the mice, to treat the pain associated with the incision. The procedure for each mouse usually lasted about ten minutes, and the inventors put the mouse back into the anesthesia chamber for up to two hours to receive the rest of the anesthesia consisting of 1.4% isoflurane in 100% oxygen. The inventors maintained the rectal temperature of the mice at 37±0.5° C. during the anesthesia/surgery by using DC Temperature Control System (FHC, Bowdoinham, Maine). The inventors returned the mice back to their home cage with food and water available ad libitum after recovering from the anesthesia. The mice in the control group were placed in their home cages with regular room air for two hours, which was consistent with the condition of non-surgery patients. The inventors' previous studies found that neither the surgery nor anesthesia with 1.4% isoflurane significantly disturbed the blood pressure, blood gas values of the mice. EMLA could treat the pain associated with the surgery in the mice.

WS-635 Treatment

WS-635 (also known as SCY-635) was dissolved in corn oil with 10% DMSO, each of the mice will be injected with WS-635 solution in the dose of 52.8 mg/kg, 26.4 mg/kg or 13.2 mg/kg, respectively, for 0.2 ml through IP at 30 minutes before, 24 hours after and 48 hours after control condition or anesthesia/surgery by using 27G×½ needles. The mice in control group received 0.2 ml of corn oil with 10% DMSO.

Barnes Maze Test

One week after anesthesia/surgery, animals were subjected to Barnes maze to test their spatial learning and memory. Barnes maze is a circular platform with 20 equally spaced holes (SD Instruments, San Diego, CA). One hole is connected to a dark chamber called target box. Each time, animals were placed in the middle of the platform and encouraged to find the target box by aversive noise (85 dB) and bright light (200 W) shed on the platform. They went through a spatial acquisition phase that consists of training on 4 days with 2 trials per day, 3 minutes per trial and 15 minutes between each trial. The latency and number of errors to find the target box during each trial were recorded with the assistance of ANY-Maze video tracking system.

Diagram of the experimental design is shown in FIG. 1.

Fear Conditioning Test (FCT)

The FCT was performed as those described by Saab et al. with modification. Specifically, WT mice (8-month-old) were randomly assigned to either the anesthesia or the control group. The pairing in FCT (Stoelting Co., Wood Dale, IL) was performed at two hours after the isoflurane or desflurane anesthesia. Each mouse was allowed to explore the FCT chamber for 180 seconds before presentation of a 2-Hz pulsating tone (80 dB, 3,600 Hz) that persisted for 60 seconds. The tone was followed immediately by a mild foot shock (0.8 mA for 0.5 second). The first context test was performed at 30 minutes after the end of the pairing. Each mouse was allowed to stay in the chamber for a total of 390 seconds. Function of learning and memory in the context test was assessed by measuring the amount of time the mouse demonstrated "freezing behavior", which is defined as a completely immobile posture except for respiratory efforts during the second 180 seconds.

The first tone test was performed at 90 minutes after the end of the pairing. Each mouse was allowed to stay in the chamber for a total of 390 seconds. The same tone was presented for the second 180 seconds without the foot shock. Function of learning and memory in the tone test was assessed by measuring the amount of time the mouse demonstrated "freezing behavior", defined as a completely immobile posture except for respiratory efforts, during the second 180 seconds. The second and third context and tone tests were performed at 48 hours and 7 days after the anesthesia, respectively. The "freezing behavior" was analyzed by Any-Maze (freezing on threshold: 10; freezing off threshold: 20; minimum freezing duration: one second) (Stoelting). The percentage of freezing time was calculated by dividing the actual freezing time with the observed time (180 seconds).

Figure 2:
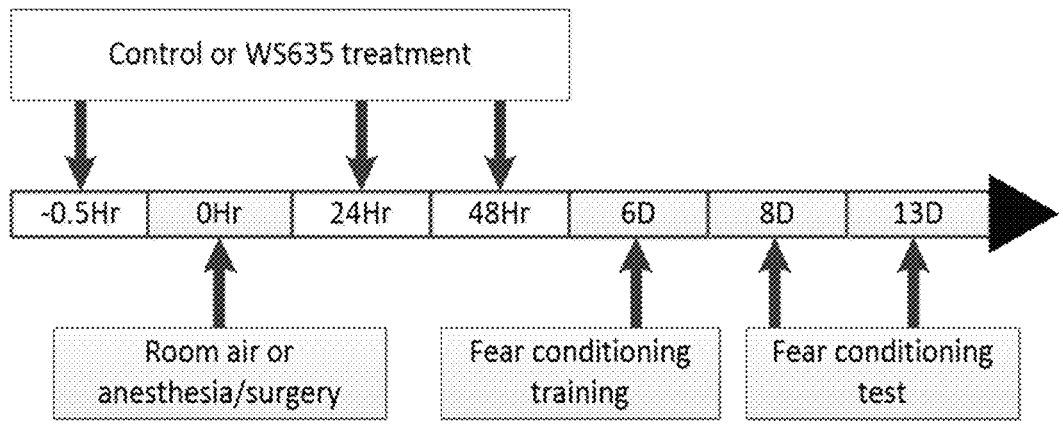
FIG. 2 shows the diagram of the experimental design (Fear Conditioning Test)

Diagram of the experimental design is shown in FIG. 2.

Brain Tissue Harvest, Lysis and Protein Quantification. Different mice will be used for the harvest of brain tissue. Levels of interleukin-6 (IL-6) and postsynaptic density (PSD)-95 in the cortex and hippocampus of mice will be assessed. The brain tissues (cortex and hippocampus) of the mice will be harvested immediately at the end of the anesthesia/surgery by decapitation. The harvested brain tissues will be homogenized on ice using immunoprecipitation buffer (10 mM Tris-HCl, pH 7.4, 150 mM NaCl, 2 mM EDTA, 0.5% Nonidet P-40) plus protease inhibitors (1 mg/ml aprotinin, 1 mg/ml leupeptin, 1 mg/ml pepstatin A). The lysates will be collected, centrifuged at 10,000 rpm for 5 minutes at 4° C., and quantified for total proteins by bicinchoninic acid (BCA) protein assay kit (Pierce, Iselin, NJ). The brain tissues will then be subjected to Western Blot.

Western Blot Analysis. Synaptophysin antibody (1:50,000, Abcam, Cambridge, MA) was used to detect synaptophysin (molecular weight of 38 kDa). PSD-95 antibody (1:1,000, Cell Signaling, Danvers, MA) was used to detect PSD-95 (95 kDa). Antibody anti-β-Actin (1:5,000, Sigma, St. Louis, MO) was used to detect β-Actin (42 kDa). Western blot quantification was performed as described. Briefly, signal intensity was analyzed using a Bio-Rad (Hercules, CA) image program (Quantity One). The inventors quantified Western blots in two steps, first, the inventors used β-Actin levels to normalize (e.g., determine the ratio of PSD-95 to β-Actin amount) protein levels and control for loading differences in the total protein amount. Second, the inventors presented protein level changes in mice in the WS-635 treatment group as a percentage of those in the control group. One-hundred percent of protein level changes was refer to control levels for the purpose of comparison of experimental conditions.

ATP Measurement. The levels of ATP in the cortex of mice (N=6 in each group) were determined by the ATP Colorimetric/Fluorometric Assay Kit following the protocol provided by the manufacturer (Abcam, Cambridge, MA). Briefly, the brain tissues was placed in 6-well plate overnight in the incubator. The amount of fluorescence will be measured and the levels of ATP in the experimental samples will be calculated from the standard curve made from samples containing a known amount of ATP.

Righting Reflex assessment. 9-month-old C57BL/J6 female mice were adaptive in lab for 3 days. Righting reflex was assessed by placing the mouse on its back. The mice were randomly assigned to the WS-635+DMSO group (n=11), DMSO group (n=11) and Saline group (n=12). WS-635 was dissolved in corn oil with 10% DMSO, each of the WS-635+DMSO group mice was injected with WS-635 solution in the dose of 52.8 mg/kg for 0.2 ml through IP at 30 minutes before anesthesia. Each of the DMSO group mice will be injected with 10% DMSO in corn oil for 0.2 ml through IP at 30 minutes before anesthesia. Each of the Saline group mice was injected with 0.9% saline solution for 0.2 ml through IP at 30 minutes before anesthesia. The inventors anesthetized each of the mice using Isoflurane, Sevoflurane or Desflurane. Anesthetizing each of the mice using isoflurane as follows: starting at 0.0% with 0.1% step size of end-tidal isoflurane in 30% oxygen, each step maintained 15 minutes till 1.4%. Anesthetizing each of the mice using sevoflurane as follows: starting at 0.0%, then 0.5% and 1.0%, then with 0.1% step size of end-tidal sevoflurane in 30% oxygen; each step maintained 15 minutes till 2.5%. Anesthetizing each of the mice using desflurane as follows: starting at 0.0%, then 1.5% and 3.2%, then with 0.1% step size of end-tidal desflurane in 30% oxygen; each step maintained 15 minutes till 5.2%. Same mouse received each anesthetic on D1, D3 and D5.

Results

WS-635 (Also Known as SCY-635) is Able to Attenuate the Anesthesia/Surgery-Induced Changes in Brain Levels of PSD-95 and Synaptophysin.

Figure 3:
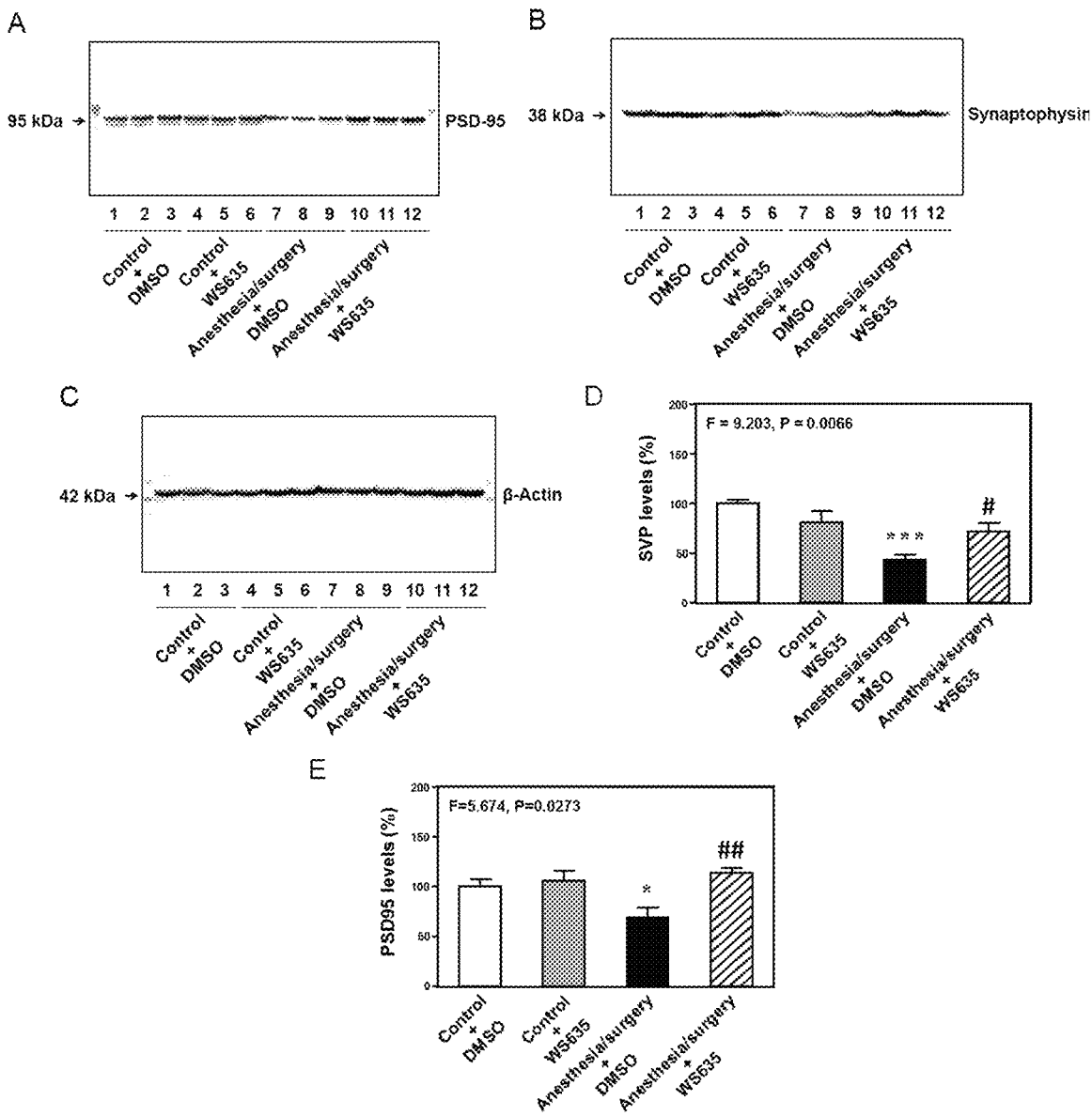
FIG. 3 shows WS-635 is able to attenuate the anesthesia/surgery-induced changes in cortex levels of PSD-95 and synaptophysin (Western Blot Analysis—Cortex)
Figure 4:
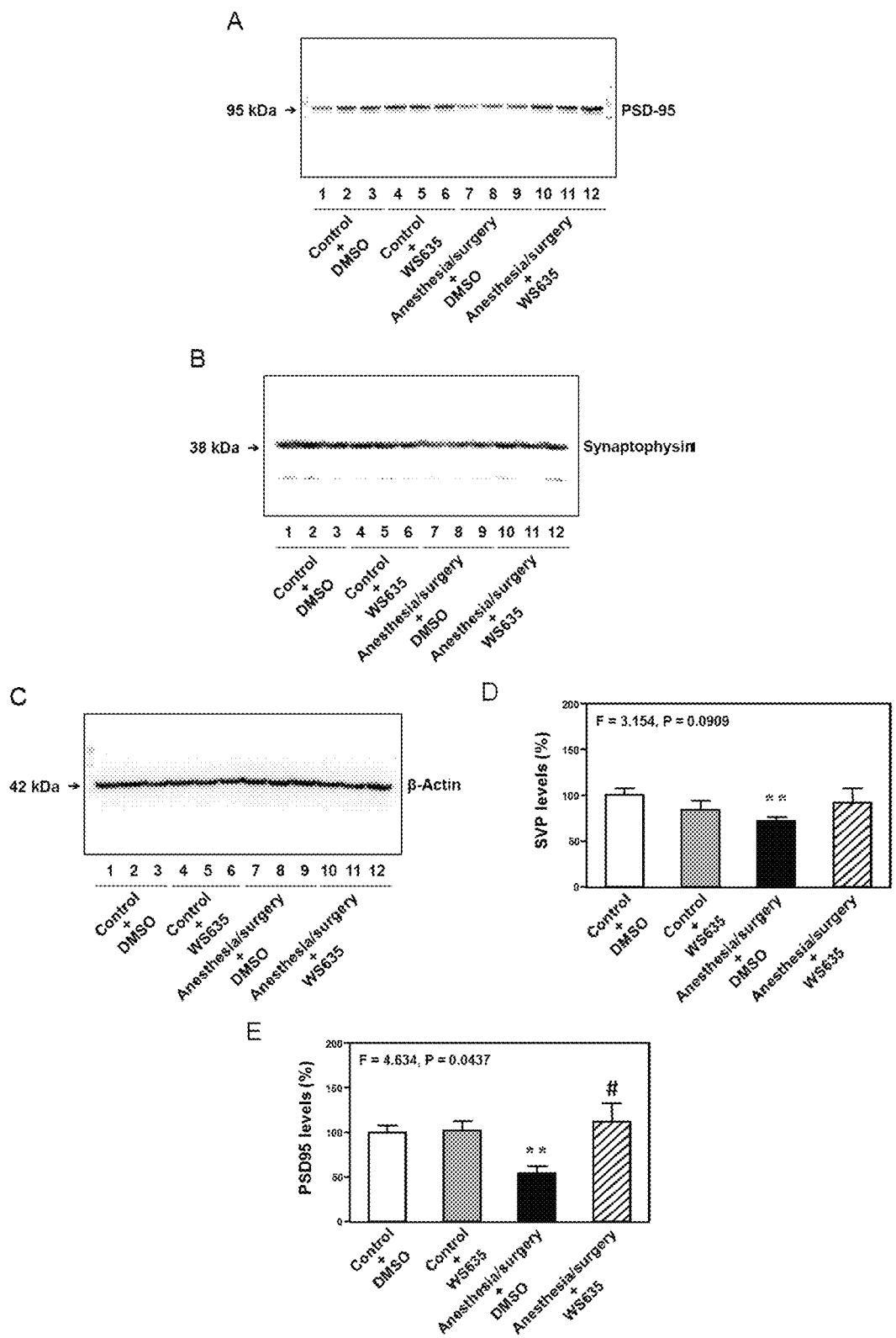
FIG. 4 shows WS-635 is able to attenuate the anesthesia/surgery-induced changes in hippocampus levels of PSD-95 and synaptophysin (Western Blot Analysis—Hippocampus)

The anesthesia/surgery will decrease PSD-95 and synaptophysin levels in both cortex (as shown in FIG. 3) and hippocampus (as shown in FIG. 4). Treatment with 26.4 mg/kg WS-635 mitigate these anesthesia/surgery-induced changes.

WS-635 (Also Known as SCY-635) is Able to Attenuate the Anesthesia/Surgery-Induced Changes in Brain Levels of ATP.

Figure 5:
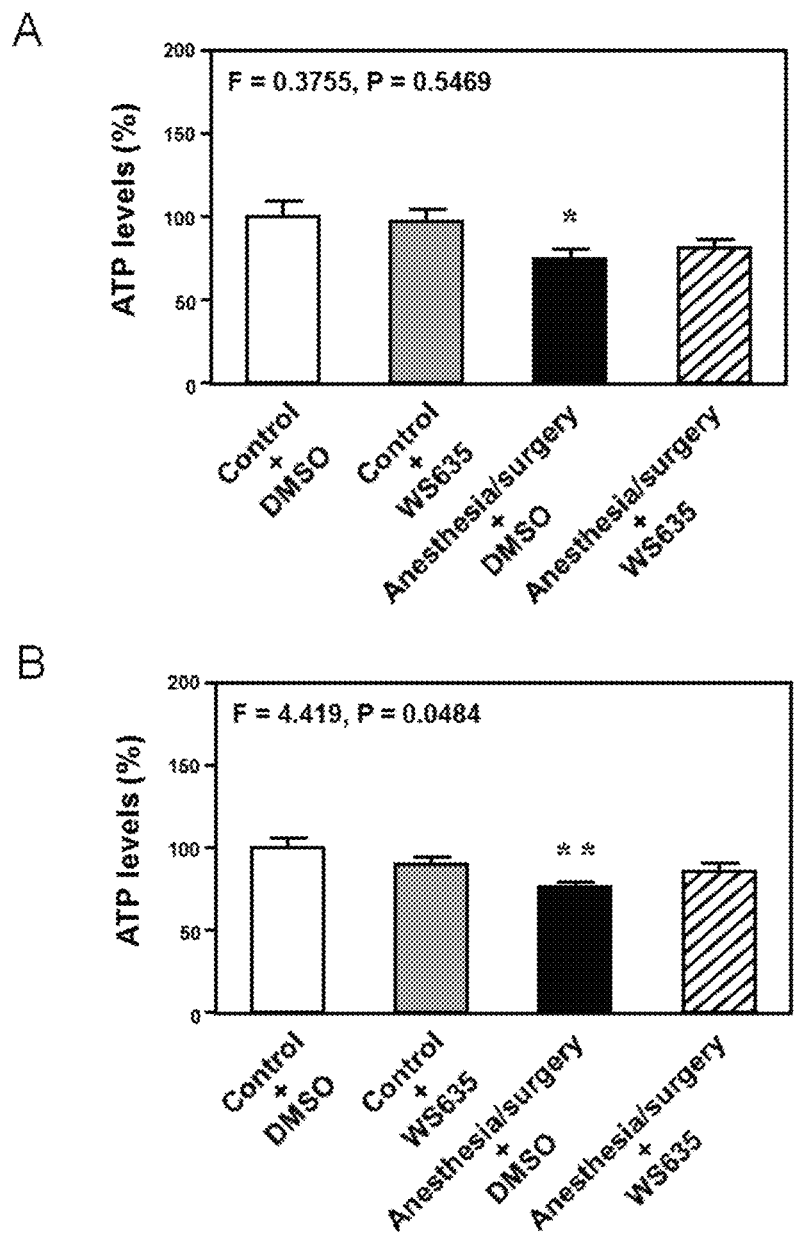
FIG. 5 shows WS-635 is able to attenuate the anesthesia/surgery-induced changes in brain levels of ATP (Cortex and Hippocampus)
Figure 6A:
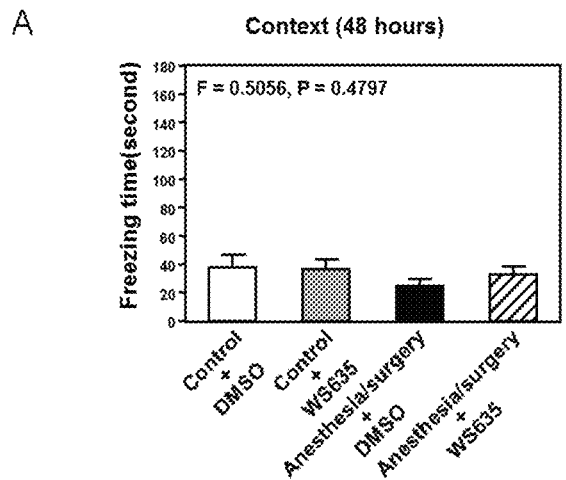
FIG. 6A~FIG. 6D show WS-635 is able to attenuate the anesthesia/surgery-induced cognitive impairment in mice (Fear Conditioning Test, 52.8 mg/kg dose)
Figure 6B:
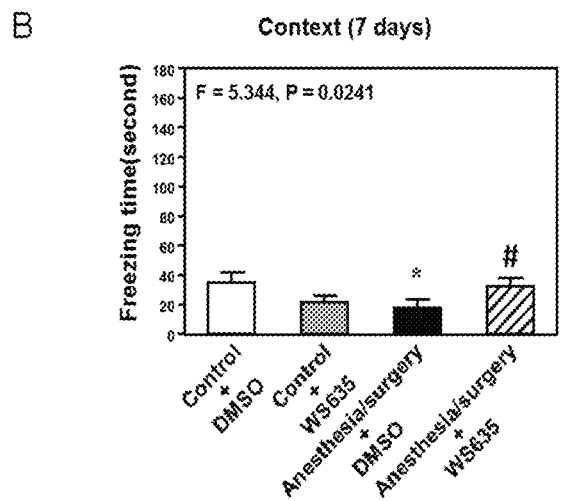
Figure 6C:
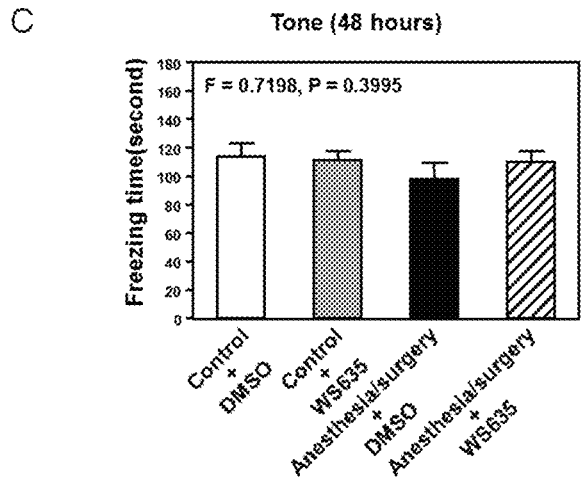
Figure 6D:
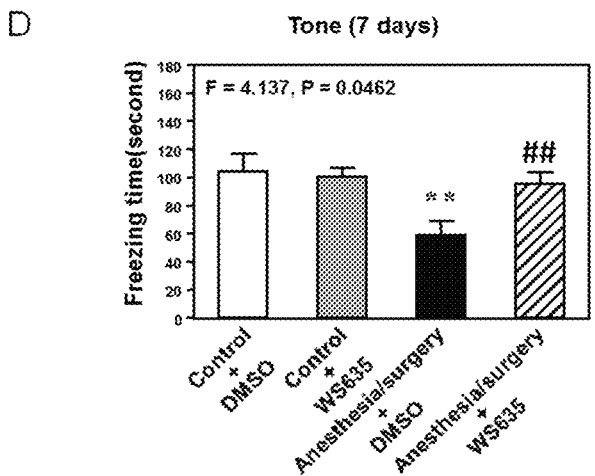
Figure 7A:
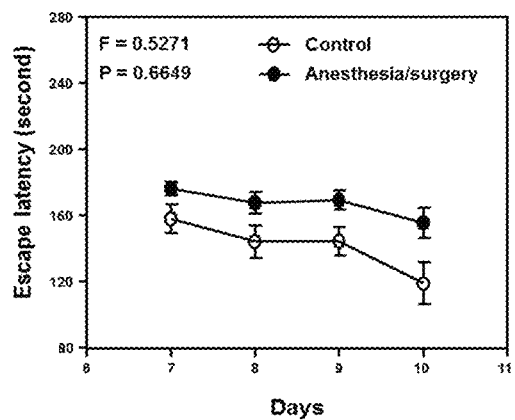
FIG. 7A~7J show WS-635 is able to attenuate the anesthesia/surgery-induced cognitive impairment in mice (Barnes Maze Test, 26.4 mg/kg and 13.2 mg/kg doses)
Figure 7B:
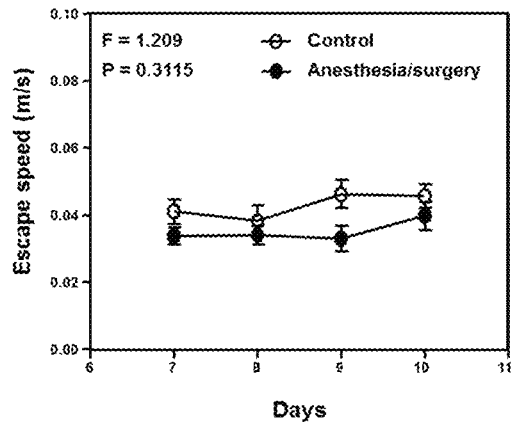
Figure 7C:
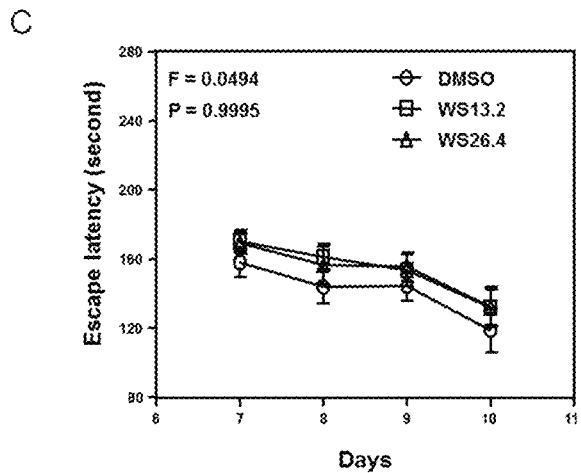
Figure 7D:
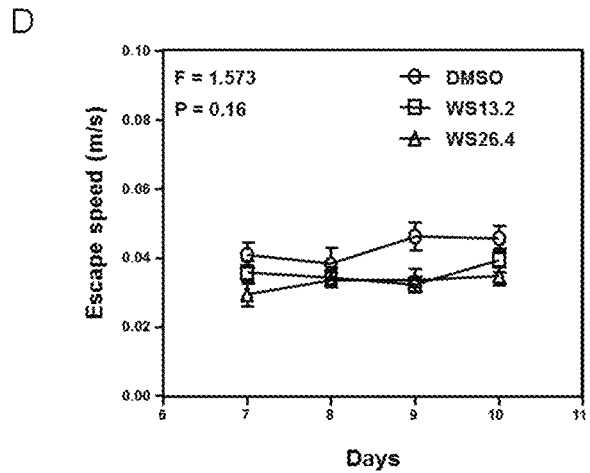
Figure 7E:
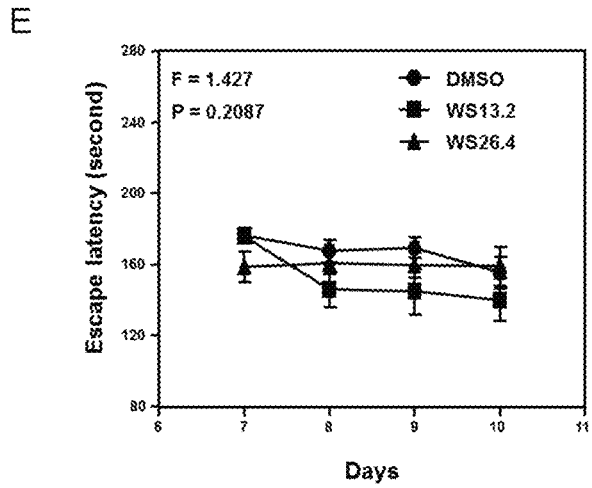
Figure 7F:
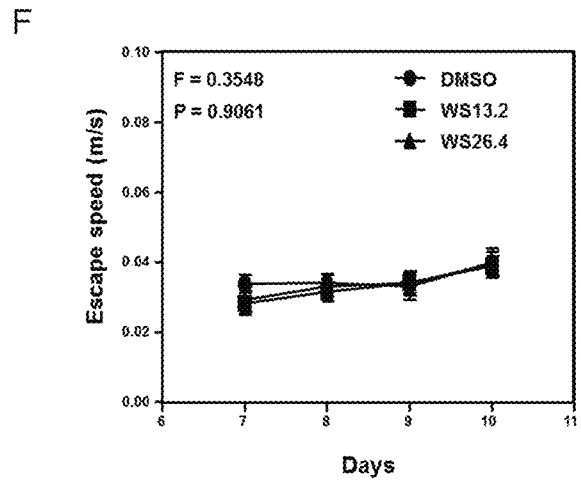
Figure 7G:
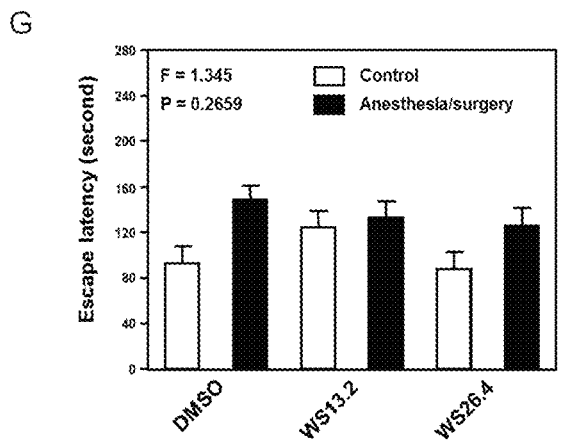
Figure 7H:
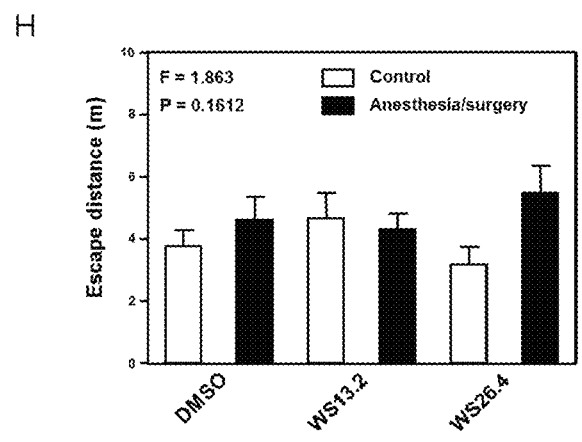
Figure 7I:
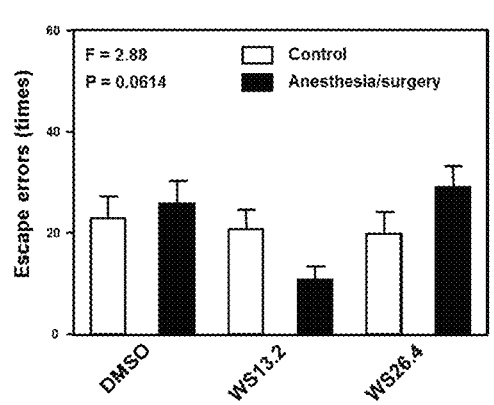
Figure 7J:
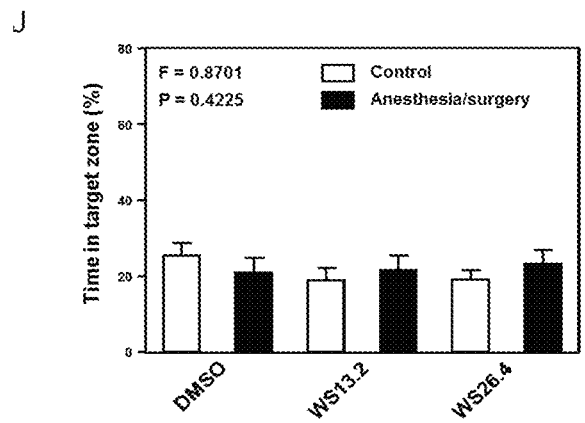

The anesthesia/surgery will decrease ATP levels in both cortex and hippocampus (as shown in FIG. 5, A shows ATP levels in cortex, B shows ATP levels in hippocampus). Treatment with 26.4 mg/kg WS-635 mitigate these anesthesia/surgery-induced changes.

WS-635 (Also Known as SCY-635) is Able to Attenuate the Anesthesia/Surgery-Induced Cognitive Impairment in Mice.

WS-635 mitigated the anesthesia/surgery-induced reduction in freezing time of mice in Fear Conditioning Test (FIG. 6A~FIG. 6D). The FIG. 6A~FIG. 6D show isoflurane or desflurane significantly decreased the freezing time of mice in Tone test of FCT at 48 hours after the anesthesia/surgery and also significantly decreased the freezing time of mice in Context test of FCT at 7 days after the anesthesia/surgery. However, WS-635 mitigated the anesthesia/surgery-induced reduction in freezing time of mice in FCT.

WS-635 mitigated the anesthesia/surgery-induced increase in escape latency and decrease in escape speed in Barnes Maze Test as compared to control condition (FIG. 7A~7J). FIG. 7A~7J show isoflurane or desflurane significantly increased the escape latency and decreased the escape speed of mice in Barnes Maze Test one week after the anesthesia/surgery. However, WS-635 mitigated the anesthesia/surgery-induced increase in escape latency and decrease in escape speed in Barnes Maze Test.

WS-635 (Also Known as SCY-635) Does not Affect the Potency of the Anesthetics.

The hypnotic action of inhalation anesthetics and the impact of WS-635 was estimated by assessing the effect on the EC50 for loss of the righting reflex (EC50-LORR). EC50-LORR was defined as the midpoint between the highest concentration at which righting reflexes existed and the lowest concentration at which righting reflexes disappeared in mice.

Figure 8:
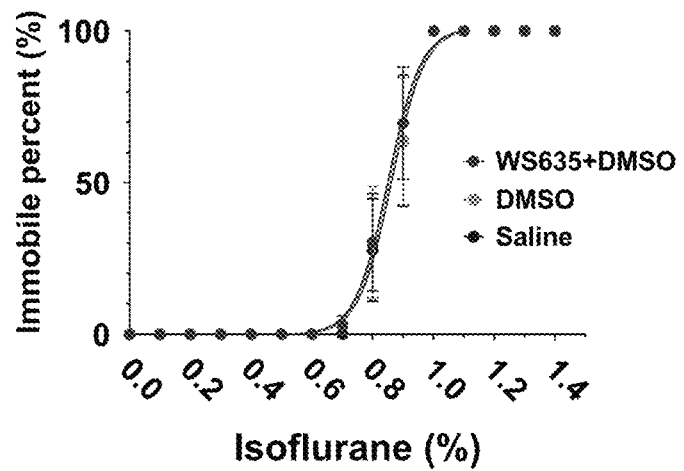
FIG. 8 shows righting reflex assessment results of mice after isoflurane anesthesia comparing treatments of WS-635+DMSO, DMSO and Saline (average of results in FIG. 9)
Figure 9:
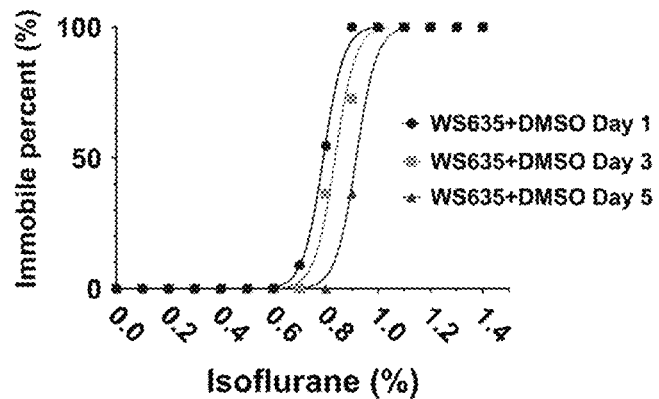
FIG. 9 shows righting reflex assessment results of mice after isoflurane anesthesia with treatments of WS-635+DMSO, DMSO and Saline on D1, D3 and D5.
Figure 9:
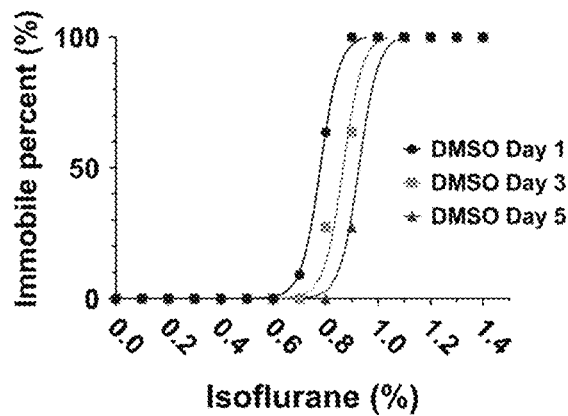
Figure 9:
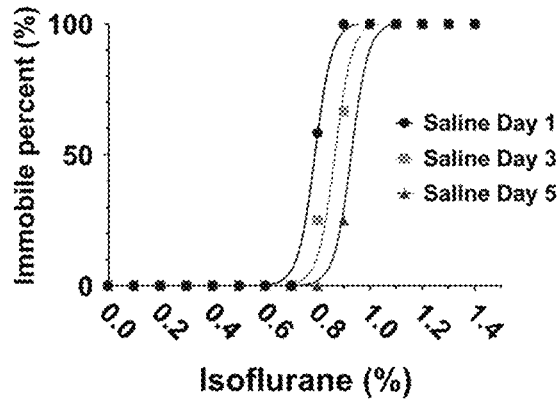
Figure 10:
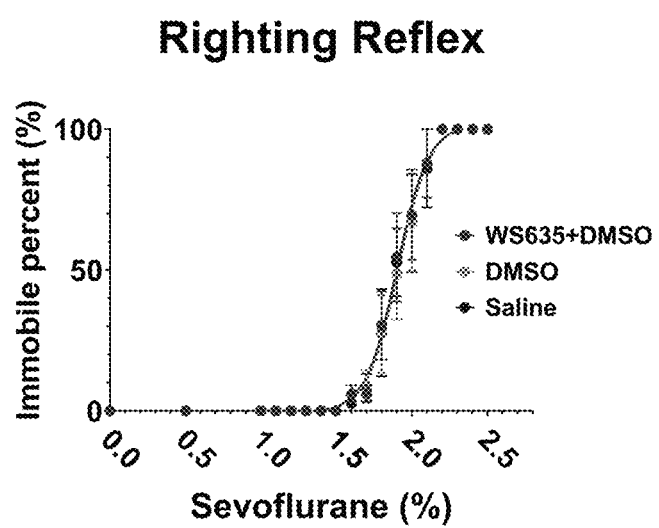
FIG. 10 shows righting reflex assessment results of mice after sevoflurane anesthesia comparing treatments of WS-635+DMSO, DMSO and Saline (average of results in FIG. 11)
Figure 11:
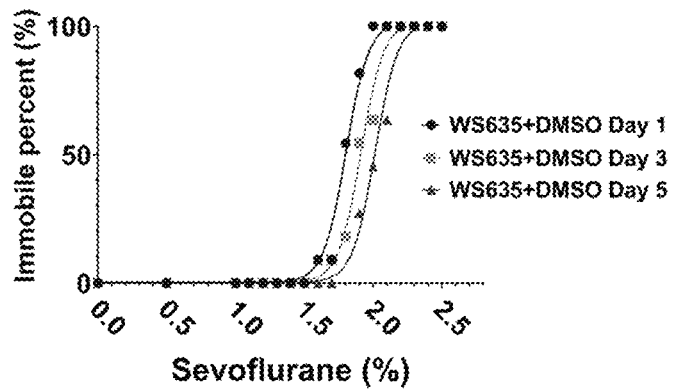
FIG. 11 shows righting reflex assessment results of mice after sevoflurane anesthesia with treatments of WS-635+DMSO, DMSO and Saline on D1, D3 and D5.
Figure 11:
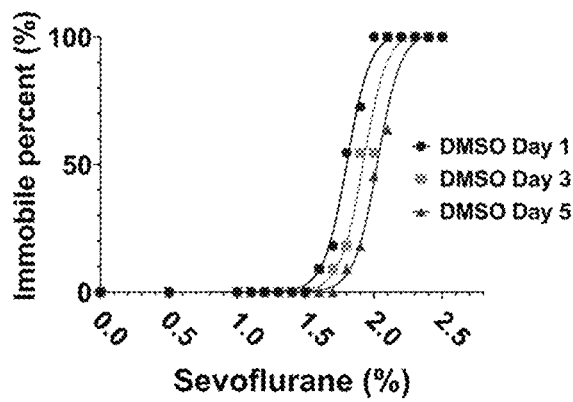
Figure 11:
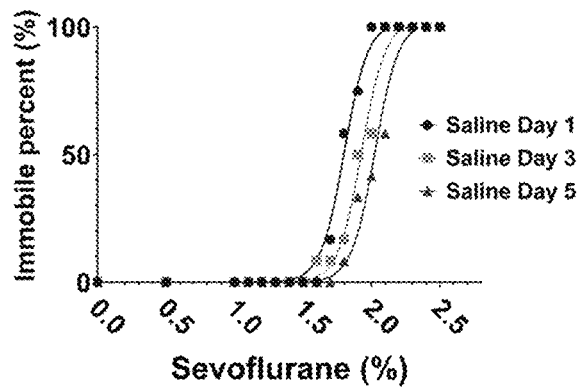
Figure 12:
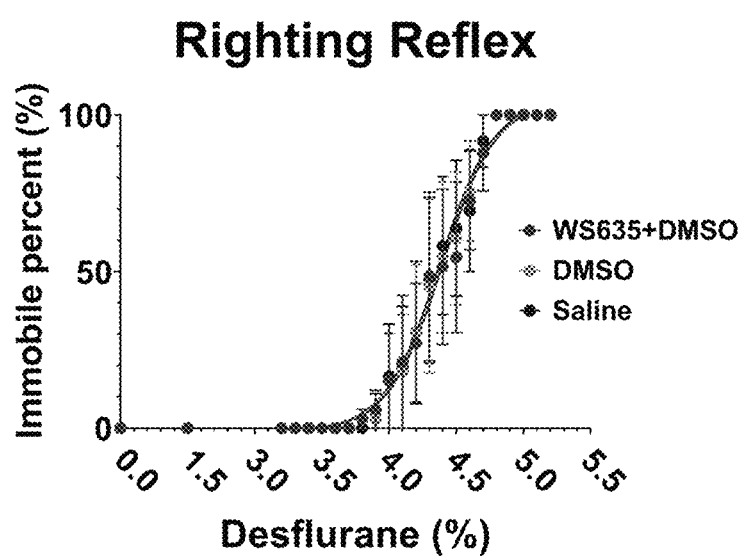
FIG. 12 shows righting reflex assessment results of mice after desflurane anesthesia comparing treatments of WS-635+DMSO, DMSO and Saline (average of results in FIG. 13)
Figure 13:
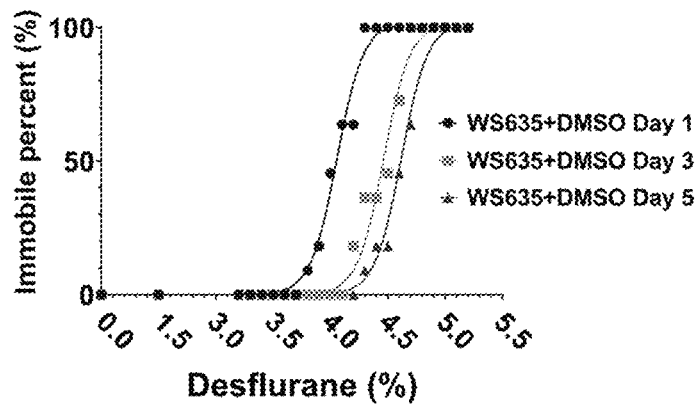
FIG. 13 shows righting reflex assessment results of mice after desflurane anesthesia with treatments of WS-635+DMSO, DMSO and Saline on D1, D3 and D5.
Figure 13:
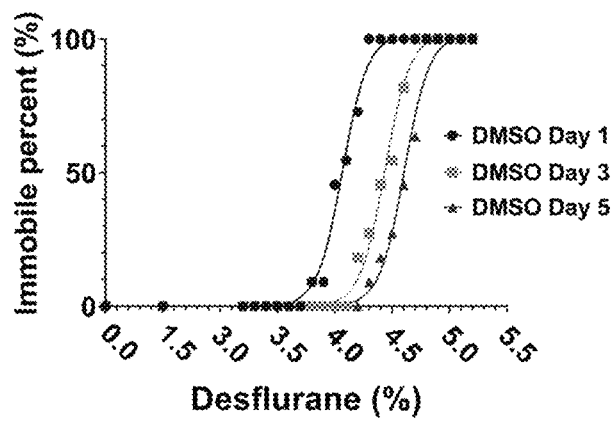
Figure 13:
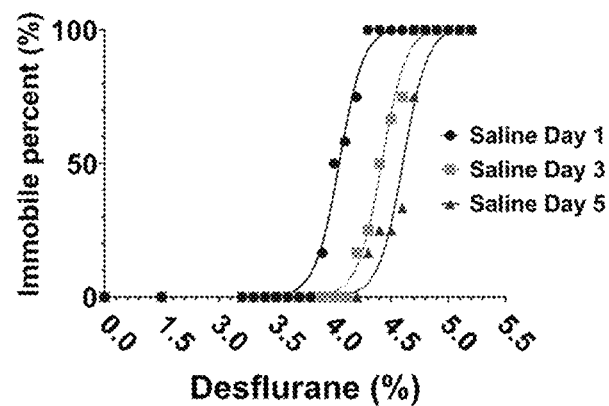

Righting reflex assessment results are shown in FIG. 8~13. These are concentration response curve of isoflurane, sevoflurane and desflurane. Y-axis represents the percent of loss of the righting reflex in mice (LORR). X-axis represents the concentration of inhalation anesthetics. The curve represents the percent of LORR in mice at each concentration of inhalation anesthetics. Wherein FIGS. 8 and 9 show the results of mice after isoflurane anesthesia. Wherein FIGS. 10 and 11 show the results of mice after sevoflurane anesthesia. Wherein FIGS. 12 and 13 show the results of mice after desflurane anesthesia. Same mouse received anesthetic on D1, D3 and D5 (FIGS. 9, 11 and 13), the EC50-LORR of each anesthetic exposure in each mice was averaged (FIGS. 8, 10 and 12) to avoid the impact of individual differences on results.

FIG. 8~13 show that WS-635 does not affect the potency of the anesthetics.

These data suggest that the treatment with WS-635 is able to mitigate the cognitive impairment induced by the anesthesia and surgery in mice. The outcomes from the animal studies indicate that WS-635 has good prospects for clinical application in treating the postoperative neurocognitive disorder in patients.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

What is claimed is:

1. A method of treating, preventing, or lessening postoperative cognitive dysfunction (POCD) in a subject in need thereof, the method comprising the step of administering to the subject a therapeutically effective amount of a compound of Formula I or a stereoisomer, a tautomer, an N-oxide, a solvate, a pharmaceutically acceptable salt or a prodrug thereof,

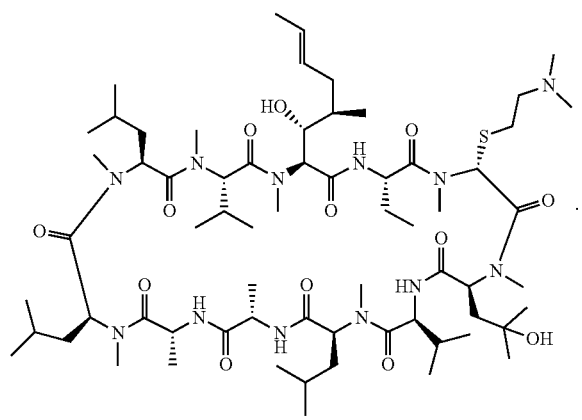

(I)

2. The method of claim 1, wherein the postoperative cognitive dysfunction is isoflurane-induced, desflurane-induced, sevoflurane-induced or propofol-induced.

3. The method of claim 1, wherein the compound is administered to the subject within 48 hours prior to the operation.

4. The method of claim 1, wherein the compound is administered to the subject within 24 hours prior to the operation.

5. The method of claim 1, wherein the compound is administered to the subject within 48 hours after the operation.

6. The method of claim 1, wherein the compound is administered to the subject within 24 hours after the operation.

7. The method of claim 1, wherein the compound is administered at a daily dose of less than about 900 mg.

8. The method of claim 1, wherein the compound is administered at a daily dose of between about 10 to about 900 mg.

9. The method of claim 1, wherein the compound is administered at a daily dose of between about 50 to about 600 mg.

10. The method of claim 1, wherein the compound is administered 1 time per day.

11. The method of claim 1, wherein the compound is administered 1 time per day as a single dosage.

12. The method of claim 1, wherein the compound is administered by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intraperitoneally and intrathecally.

13. The method of claim 1, wherein the compound is administered orally or intravenously.

14. The method of claim 1, wherein the compound is administered in a form of tablet, capsule or injection.

15. The method of claim 1, wherein the compound is administered in combination with one or more other agent used for preventing, treating or lessening cognitive impairment other than the compound of Formula I.

16. The method of claim 15, wherein the other agent comprises a coenzyme.

17. The method of claim 16, wherein the coenzyme comprises coenzyme $Q_{10}$.

* * * * *

UNITED STATES PATENT AND TRADEMARK OFFICE
CERTIFICATE OF CORRECTION

| | | |
|---|---|---|
| PATENT NO. | : 12,226,446 B2 | Page 1 of 1 |
| APPLICATION NO. | : 17/429667 | |
| DATED | : February 18, 2025 | |
| INVENTOR(S) | : Faming Zhang et al. | |

It is certified that error appears in the above-identified patent and that said Letters Patent is hereby corrected as shown below:

On the Title Page

Item (*), should read:
--(*) Notice: Subject to any disclaimer, the term of this patent is extended or adjusted under 35 U.S.C. 154(b) by 857 days.
This patent is subject to a terminal disclaimer--.

Item (45), insert:
--(*)-- before Feb. 18, 2025.

Signed and Sealed this
Twenty-sixth Day of August, 2025

Coke Morgan Stewart
*Acting Director of the United States Patent and Trademark Office*